United States Patent [19]

Benusa et al.

[11] Patent Number: 4,525,156
[45] Date of Patent: Jun. 25, 1985

[54] METHOD FOR STOMACH LAVAGE

[76] Inventors: John E. Benusa, 1383 Temple Hills Dr., Laguna Beach, Calif. 92651; Richard L. Kingston, 1577 E. 6th St., St. Paul, Minn. 55106

[21] Appl. No.: 439,751

[22] Filed: Feb. 16, 1983

[51] Int. Cl.³ .............................................. A61M 1/00
[52] U.S. Cl. ...................................... 604/28; 604/30; 604/32
[58] Field of Search .................................. 604/28–34, 604/248, 93, 96, 49, 50, 53–57

[56] References Cited

U.S. PATENT DOCUMENTS

| | | | |
|---|---|---|---|
| 2,027,588 | 1/1936 | Hannon | 604/30 |
| 3,780,736 | 12/1973 | Chen | 604/32 |
| 4,114,625 | 9/1978 | Onat | 604/96 |
| 4,219,021 | 8/1980 | Fink | 604/93 |
| 4,240,408 | 12/1980 | Schael | 604/29 |
| 4,319,569 | 3/1982 | Hu | 604/333 |
| 4,403,982 | 9/1983 | Clayton | 604/28 |

OTHER PUBLICATIONS

Attorneys' Dictionary of Medicine and Word Finder, J. E. Smidt, M.D., vol. 2, Matthew Bender, New York, N.Y., 1980, "Lavage".

Primary Examiner—C. Fred Rosenbaum
Assistant Examiner—J. L. Kruter
Attorney, Agent, or Firm—Willie Krawitz

[57] ABSTRACT

A sanitary, disposable, gastric lavage closed system is disclosed that quickly and effectively flushes material from a patient's stomach. The system includes an elevated, plastic reservoir bag connected through a feed line having a specified bore range, to a T-connection. A gastric tube is fitted to the T-connection and is adapted for insertion into the patient's stomach. A fixed volume of liquid from the reservoir bag is admitted to the patient by pump or by hand control of the feed line over a short, measured period of time.

Material in the patient's stomach is then quickly removed into a disposable container that forms a closed system with the rest of the components.

An injection syringe may be employed to inject treatment materials into the stomach, remove test samples, and maintain the system free of clogged material.

An attachment for colonic irrigation and enemas may be employed to replace and/or by-pass the gastric tube.

10 Claims, 4 Drawing Figures

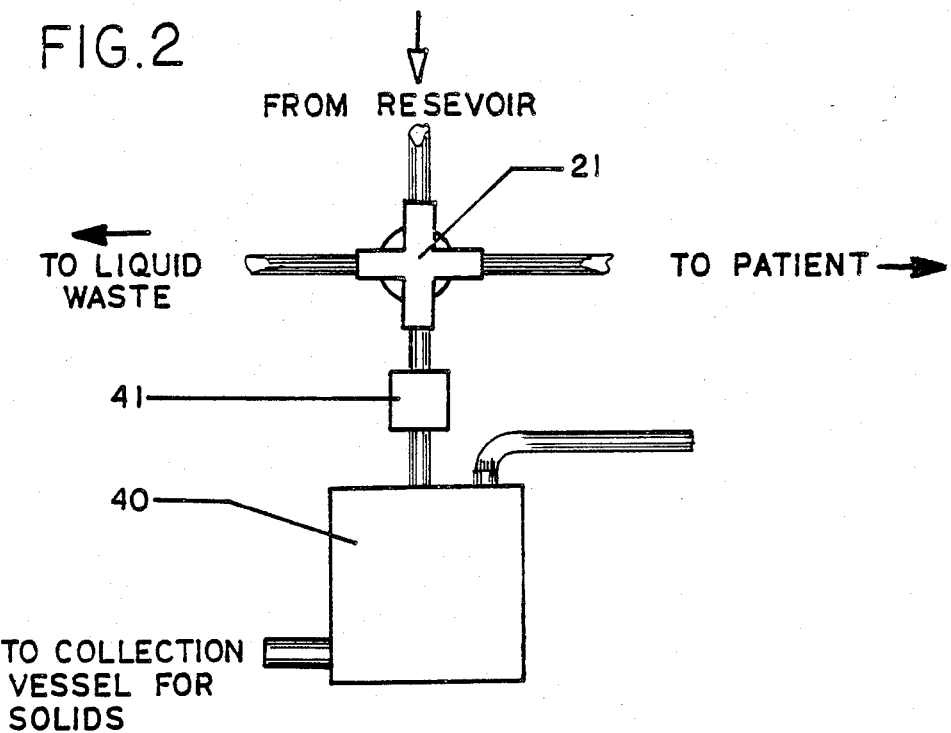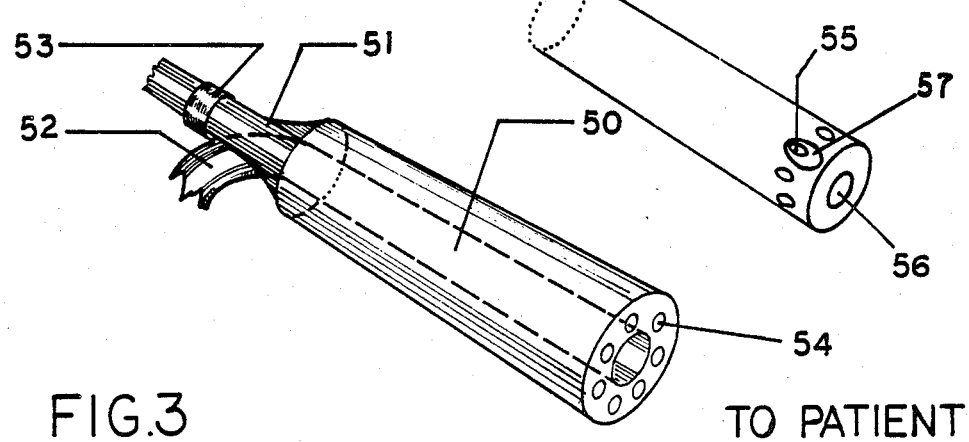

METHOD FOR STOMACH LAVAGE

BACKGROUND OF THE INVENTION

This invention relates to a new and improved lightweight, gastric lavage system, and more specifically to a disposable gastric lavage system that can quickly dispense a fixed quantity of liquid into a patient's stomach and remove the material therefrom in a sanitary manner.

Various publications disclose the use of gastric lavage systems, and typical ones include: U.S. Pat. Nos. 386,603; 1,349,766; 2,919,695 3,233,609; 3,756,237; 3,885,567; and, 4,190,059.

Other publications in this field include: "New Tube For The Diagnosis and Treatment of Upper Gastrointestinal Hemorrhage", by Paul Robert Liebman and Yanek S. Y. Chiu, presented at the Twenty-Second Annual Symposium of the Society of Air Force Clinical Surgeons, Apr. 8-10, 1974, Los Vegas, Nev.; "Gastric Lavage For Hemorrhage In The Upper Part Of The Gastrointestinal Tract", by Robert Joseph Atkenson and Lloyd M. Nyhus, Surgery, Gynecology & Obstetrics, 798, May 1978, Vol 146; "Comparison Of Ice Water With Iced Saline Solution For Gastric Lavage In Gastroduodenal Hemorrhage" by Bryant, Mobin-Uddin, Dillon and Griffen, The American Journal of Surgery, Vol. 124, November 1972, Page 570; and, "Gastric Aspiration and Lavage in Acute Poisoning", by atthew, Mackintosh, Tompsett and Cameron, BR.MED.J.1966,1,1333–1337.

One type of stomach lavage discloses the use of a stainless steel reservoir to supply a fixed amount of fluid to the stomach of a patient as determined by a pressure device. However, this system is heavy and expensive, and consequently it is not feasible to maintain a large number of these devices available for immediate and ready use. Also, the device is not readily portable.

Certain types of lavage systems are used to obtain an initial diagnosis of internal stomach bleeding, while other types of lavage systems are designed to simply remove the contents of a patient's stomach. It would be advantageous to provide a device that can both diagnose bleeding and obtain a stomach lavage.

Most, if not all, types of lavages take a long time to dispense liquid, and this of course is detrimental to the patient. It would be preferable to quickly dispense liquid to a patient's stomach and in accurate volumes, to avoid a liquid overdose.

Most treatments with stomach lavage devices involve overdose patients, patients who suffer from poisoning, patients who are experiencing stomach hemorrhaging, those who are suffering from gastroenteritis, and the like. Hence, it is desirable, particularly in these cases, to minimize odors, spilled gastric liquids, etc. Consequently, a closed or semi-closed system is necessary to achieve these results. A closed system would also reduce the risk of contamination and spreading of disease such as hepatitis and reduce contaminating the patient with hospital associated substances and diseases. This is especially the case where enemas or colonic irrigations are administered and the patient is bedridden. Here, the risk of contamination is even greater.

In addition, considering the expense of storage space and the time and expense of sterilization it is preferred to provide a lightweight disposable lavage system that is not restricted by weight, use or expense to a specific area in a hospital.

Also, a lavage system is desired that is simple to use and can be set up, manipulated and removed quickly and easily.

It will be appreciated that quite frequently, an analysis of the contents of a patient's stomach is necessary to effect prompt treatment once the stomach contents are removed. Hence, it is essential that fairly large size objects be removed without obstructing or clogging the device.

If the stomach lavage device also is to be used for a patient who may be hemorrhaging, the device should not produce red suction bruises on the stomach wall since these marks may be confused with hemorrhaging sites during subsequent viewing with a probe, and may worsen the patient's condition.

The device should be capable of readily monitoring the amount of fluid administered to, and removed from a patient. Additionally, a device that can fulfill the dual function of a gastric lavage and a colonic irrigation, or for enemas is desired.

THE INVENTION

According to the invention, a disposable, closed, gastric lavage system is provided having a graduated, closable, plastic reservoir adapted for use in an elevated position above a patient. A feed line, preferably of plastic, is attached to the exit of the reservoir and the bore of the feed line is sized to pass a specific volume of liquid being administered to the patient. The end of the feed line is attached to a 180° double-T connection to obtain straight line flow. One end of the double-T is attached to a gastric lavage tube for insertion into a patient's stomach, and the other end of the double-T is connected via a discharge line to a discharge bag, usually constructed of plastic. The feed line, gastric lavage tube and discharge line are each provided with a closure element to effect flow control.

A syringe device, attached through the double-T connection, may be employed to inject medication into the stomach. If desired, hand metering can be replaced by a feed pump such as described in U.S. Pat. Nos. 3,393,673; 3,227,158; and, 3,425,410. Also, the gastric lavage tube may be replaced by a colonic irrigation or enema tube, the remainder of the system being the same; however, the reservoir size is increased.

Opening and closing the feed line from the reservoir during a specified period of time will enable the user to reasonably control the volume of liquid supplied to the patient. This can be verified by observing a graduated scale on the reservoir. This close time control over the liquid flow is achieved by sizing the bore of the feed line to enable a time monitoring of the liquid passed from the reservoir. The time constraints are imposed on the one hand by safety factors in that a too rapid flow of liquid into the stomach is undesirable, since the liquid volume is difficult to control. On the other hand, if the time of liquid flow is too lengthy, the contents of the patient's stomach will not be removed quickly enough, and the patient will suffer.

BRIEF DESCRIPTION OF THE DRAWINGS

FIG. 2 is a schematic view of a portion of the stomach lavage system in which the syringe port is replaced by a collection vessel;

FIG. 3 is an external perspective view of a colonic tube connected to a monitoring pump, fluid source and effluent line for use in stomach or colonic irrigation and/or enemas; and, FIG. 3A is an external perspective view showing a colonic tube having end perforations for adaptation of the system for use in stomach colonic irrigation and/or enemas.

DESCRIPTION OF THE PREFERRED EMBODIMENTS

Figure 1:
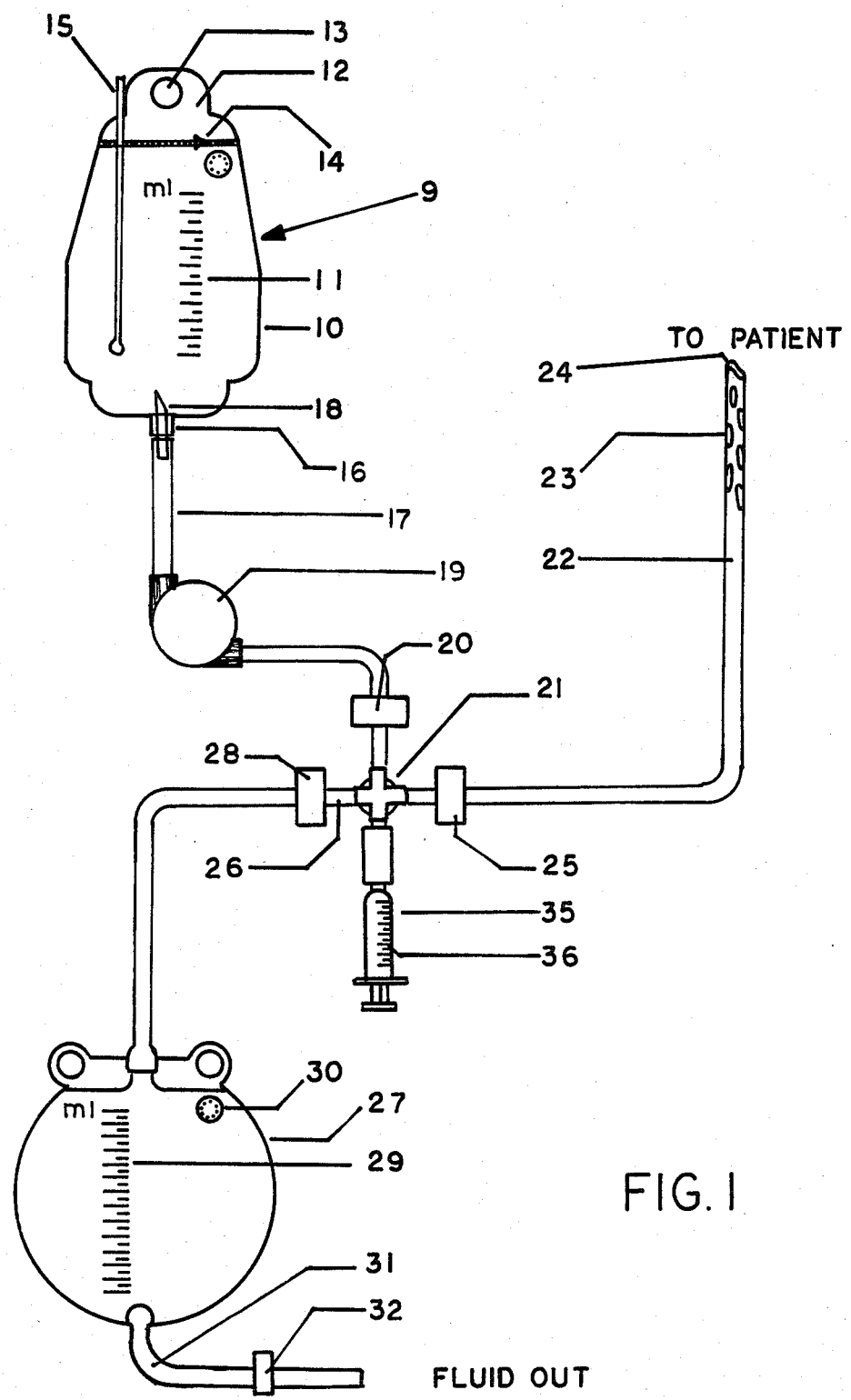
FIG. 1 is a schematic view of the stomach lavage system of this invention, including an injection syringe port.

The gastric lavage system 9 of this invention is shown in FIGS. 1 and 2, and includes a flexible liquid reservoir bag 10 of about 2-4 liters positioned above a patient. In the case of colonic irrigation or enemas, the reservoir bag is about 5 gallons in volume. The reservoir bag is typically constructed of clear polyethylene film of 4-8 mil thickness and bears a graduated scale 11 printed on the exterior. The upper end of the bag forms a tab 12 having a hole 13 for supporting on a hook (not shown). A zip lock 14 is used to maintain a relatively tight closure during storage and use to minimize contamination. A thermometer 15 is placed within the bag 10. The lower part of the bag 10 defines a hollow, sealed end fitting 16 to which is attached a feed line 17 having a hollow piercing needle 18; alternatively, a simple attachment may be used.

A volumetric pump 19 may be used to predetermine the volume of liquid supplied to the patient on the basis of time or by volume. The pump may impart pulsating flow to the liquid administered to the patient to dissolve and break up pills, clots, poisons, fecal material, etc.

Hand metering may be used instead of the pump 19, and this entails use of an on-line clamp 20 that is mounted on the feed line 17 for controlling and cutting off liquid from the reservoir. When using a feed line about 3-10 feet long, with a bore size of about 8-10 mm, an effective, hand controlled time monitoring can be made to control the volume of liquid being delivered to a patient.

An open (i.e. no Joints), 180° double-T 21 connects the feed line to a gastric lavage tube 22, the latter being inserted into the stomach of a patient. At its sides and end, the gastric tube is perforated 23, 24 to facilitate withdrawal of pills, body fluids etc. Typically, the perforations are oval shaped and measure 18/32"×8/32"; these oval perforations are shown in a spiral orientation. A convenient size of gastric tube is 40 French, and usually, the tube is constructed of polyethylene. By manipulating the gastric tube and a suction device that will be described, infra, blood clots may be removed from the stomach. An on-line clamp 25 mounted on the gastric tube 22 is adapted to control and cut off liquid from the feed line 17 and to cut off the flow of liquid to the stomach.

A discharge line 26 connected to the double-T will drain liquid from the stomach into an attached, flexible, polyethylene collection bag 27 of about 4-5 liter capacity. In the case of colonic irrigation, or for enemas, the collection bag would be of 5-10 gallon size. An on-line clamp 28 controls liquid flow through the discharge line. External graduation markings 29 on the bag 27 permits a double check on the volume of liquid passed from the reservoir bag 10 into and out of the stomach. Also, the bag 27 provides a convenient, closed system collection means. A vent 30 is formed on the bag to permit depressurizing the bag while it is being filled. A drain hose 31 and clamp 32 are attached to the bag for discharging the stomach contents to drain, or for analysis and visual inspection.

An injection syringe 35 is connected to the double-T for injection of medication, and the like into the patient via the gastric tube 22; however, its use is optional. Graduation lines 36 are marked on the exterior of the syringe to enable measuring of ingredients to the patient. The injection syringe may be omitted, as shown in FIG. 2, and replaced by a solids collector 40 connected to the double-T 21 by an adaptor 41. The feed line 17, gastric tube 22 and discharge line 26 are all connected to the double-T 21 during assembly and may be disconnected during use, due to say plugging, removal of any air pockets in the lines, etc.

Prior to use, water, ice, water, and possibly saline or other medication solution are filled into the reservoir bag 10 which is then closed along the zip lock 14 to minimize the possibility of external contamination. The gastric lavage tube 22 is then inserted into the patient's stomach and connected to the double-T. The discharge line 26 is connected to the double-T and the collection bag 27. When used, the injection syringe 35 is then mounted on the double-T.

In use, the on-line clamps 20 and 25 are opened to admit about 300-500 ml of chilled solution from the reservoir bag 10 through the feed line 17, and gastric lavage tube 22 into the patient's stomach for about 10 seconds; the two clamps are then closed. Given the bore diameter of the feed line 17, the 10 second open time of the clamps can reasonably control or calibrate the amount of water necessary for a single stomach wash. When the stomach has been filled by a single wash, the on-line clamp 28 is opened, and the liquid from the stomach is permitted to siphon out from the stomach into the collection bag 27.

The washes are repeated until about 7-8 liters of liquid are consumed. This 7-8 liter multiple washing treatment usually takes about 10-30 minutes, and preferably about 15 minutes. Each separate stomach filling treatment requires about 8-25 seconds. If a single filling treatment exceeds about 25 seconds, the overall treatment of 7-8 liters becomes too slow, while if a single treatment is faster than about 8 seconds, it is difficult to safely control the amount of liquid being administered to the patient. For a single treatment, about 300-500 ml of liquid can be administered safely in about 10 seconds; this permits a rapid overall treatment with a 7-8 liter multiple washing to be made effectively within, say 30 minutes. Using an 8-10 mm bore size feed line of about 3-10 feet in length, the liquid being administered to the patient can be hand metered; the liquid feed time can be etermined with a simple timer, wrist watch, etc.

During use, the on-line clamps 20, 25 and 28 may be closed, and any pills or materials that are present or which clog the double-T 21 may be readily removed by disconnecting the tubing from the double-T; this technique may also be used to obtain a sample for analysis. Since there is a 180° connection at the double-T between the patient side and the discharge side, there are no major portions of the system that can become clogged.

Use of the injection syringe is primarily for enabling medication such as drug or poison antidotes, activated charcoal, etc. to be supplied to the patient. However, the injection syringe 35 also can be used to loosen material in the double-T without requiring the tubing to be disconnected. Manipulation of the gastric tube then permits removal of blood clots for analysis. In short, the stomach lavage device of this invention can be used both for stomach lavage treatment and for patients with internal stomach hemorrhaging.

The embodiment of the invention shown in FIG. 3 is used for enemas and/or colonic irrigation. Essentially, the gastric lavage system is replaced by a speculum or colonic tube 50 directly connected to the pump 19 via a line 51. Effluent from the patient is passed through a line 52 to a closed discharge vessel or toilet. A pressure monitor 53 is placed on the line 51 and is designed to prevent excess liquid being administered to the patient. The monitor is designed to release fluids at about 0-2 psi, and usually at about 1.5 psi. The speculum or colonic tube 50 is typically about 6 inches long and ¾" to ⅞" in diameter. The tube 50 may have a plurality of discrete inlet end perforations 54, and an end orifice 56, as shown in FIG. 3. If desired, as shown in FIG. 3A, the tube may be provided with a plurality of inlet end perforations 55, a central outlet orifice 56, and a plurality of outlet side orifices, one such orifice 57 being shown. The perforations 55 and outlet orifices 57 are interconnected to obtain a self-cleaning system, and prevent the device from becoming plugged and causing a colon pressure build-up when in use.

The apparatus of this invention provides a simple, inexpensive lightweight construction that is readily and quickly assembled, easy to store and handle, and is disposable following use. The device and process permits a thorough stomach lavage, quickly and safely without requiring the presence of a large number of skilled personnel. Manufacturing costs are low, and the components are inexpensive.

Similarly, the use of a closed system for administering enemas, colonic irrigations, and the like, reduces or eliminates the need for toilet facilities for say bed-ridden patients, and markedly reduces contamination of the patient care areas. Since the apparatus is disposable, the possibility of subsequent infection due to inadequate sterilization of equipment is eliminated.

We claim:

1. A method for providing a closed stomach lavage, comprising the steps of:
   (a) supplying liquid by gravity feed from a flexible reservoir bag having graduations thereon, to an attached feed line having a bore size of about 8-10 mm and a length of about 3-10 feet, the feed line having manual closure means, and being connected to a connection-T;
   (b) feeding the liquid from the feed line to a connection-T and to a manually closable, multi-perforated stomach lavage tube attached to the connection-T;
   (c) supplying liquid through the lavage tube to the stomach of a patient, and manipulating the lavage tube to remove, by siphoning, foreign matter from the stomach, without the formation of red suction bruises;
   (d) siphoning the foreign matter from the stomach lavage tube to a manually closable discharge line connected to the connection-T and then to a discharge bag having an effluent line;
   the reservoir bag, feed line, lavage tube, discharge line and discharge bag being disconnectably mounted from each other and the connection-T to form a closed system;
   whereby: i. the feed line is sized to admit by hand metering, about 7-8 liters of liquid from the reservoir bag in about 10-30 minutes for multiple washings of about 300-500 ml each during a period of about 8-25 seconds; ii. by gravity feed through the lavage tube to a patient; iii. the volume of liquid admitted from the reservoir bag to the patient being correlated with the graduated scale; v. material from the stomach of the patient being siphoned through the discharge line and into the discharge bag; vi. during use, the connection-T can be disconnected to enable removal of material clogging the connection-T; vii. the closure means on the feed line and lavage tube are open and the discharge line is closed to admit liquid from the reservoir through the feed line, and to the lavage tube, and the closure means on the feed line is closed when the discharge line is open to admit material from the stomach to the discharge line and discharge bag; and, viii. following use, the lavage parts are discarded.

2. The method of claim 1, in which the reservoir and discharge bags are maintained closed during use.

3. The method of claim 1, in which the discharge bag is provided with a graduated scale to measure the volume of liquid therein, and an effluent line and clamp therefor is provided to control the volume of material leaving the discharge bag.

4. The method of claim 1, in which the reservoir bag, discharge bag, feed line, lavage tube and discharge line are constructed of a flexible plastic.

5. The method of claim 1, in which the flexible plastic is polyethylene.

6. The method of claim 1, providing an injection syringe and port to the connection-T, the injection syringe being adapted to supply medication and ice to the stomach lavage tube, and withdraw material from the patient's stomach, feed line and discharge line.

7. The method of claim 1, in which the discharge line and lavage tubes are oriented at 180° in the connection-T.

8. The method of claim 1, in which a single treatment of liquid is administered in about 10 seconds.

9. The method of claim 1, in which the total amount of liquid is administered in about 15 minutes.

10. The method of claim 1, in which a single treatment of liquid is administered in about 10 seconds, and the total amount of liquid is administered in about 15 minutes.

* * * * *